United States Patent [19]

Glover et al.

[11] Patent Number: 4,550,371

[45] Date of Patent: Oct. 29, 1985

[54] METHOD AND APPARATUS FOR COMPENSATING CT IMAGES FOR TRUNCATED PROJECTIONS

[75] Inventors: Gary H. Glover, Waukesha; Norbert J. Pelc, Milwaukee, both of Wis.

[73] Assignee: General Electric Company, Waukesha, Wis.

[21] Appl. No.: 424,501

[22] Filed: Sep. 27, 1982

[51] Int. Cl.⁴ .............................................. A61B 6/00
[52] U.S. Cl. ...................................... 364/414; 378/19; 382/54
[58] Field of Search .................. 364/414; 378/18, 901, 378/19; 382/50, 52, 53, 54

[56] References Cited

U.S. PATENT DOCUMENTS

| | | | |
|---|---|---|---|
| 4,172,978 | 10/1979 | Hounsfield et al. | 364/414 X |
| 4,228,505 | 10/1980 | Wagner | 364/414 |
| 4,305,127 | 12/1981 | Heuscher | 364/414 |
| 4,384,209 | 5/1983 | Wagner et al. | 364/414 X |
| 4,413,351 | 11/1983 | Kowalski | 364/414 X |
| 4,458,358 | 7/1984 | Klausz | 364/414 X |
| 4,472,823 | 9/1984 | Waltham | 364/414 X |

OTHER PUBLICATIONS

Lewitt, R. M., "Processing of Incomplete Measurement Data in Computed Tomography", Medical Imaging Processing Group Tech. Report MIPG22, Dept. of Computer Science, SUNY at Buffalo, Feb. 1979.

Primary Examiner—Jerry Smith
Assistant Examiner—Clark A. Jablon
Attorney, Agent, or Firm—Leydig, Voit & Mayer, Ltd.

[57] ABSTRACT

A method and apparatus for compensating CT images for truncated projections created when an object extends beyond the field of view during the course of collecting a set of projections. Projections which have reference channel information influenced by the object are identified, and the reference channel information thereof replaced by more accurate information derived from unaffected projections. The zero and first order moments of the projection set are analyzed to better estimate the expected moments had the truncated projections not been truncated, and to use that information in completing the truncated projections. A closed form solution is used for convolution of the extensions of the truncated projections to avoid substantial delays in processing the final CT image.

9 Claims, 7 Drawing Figures

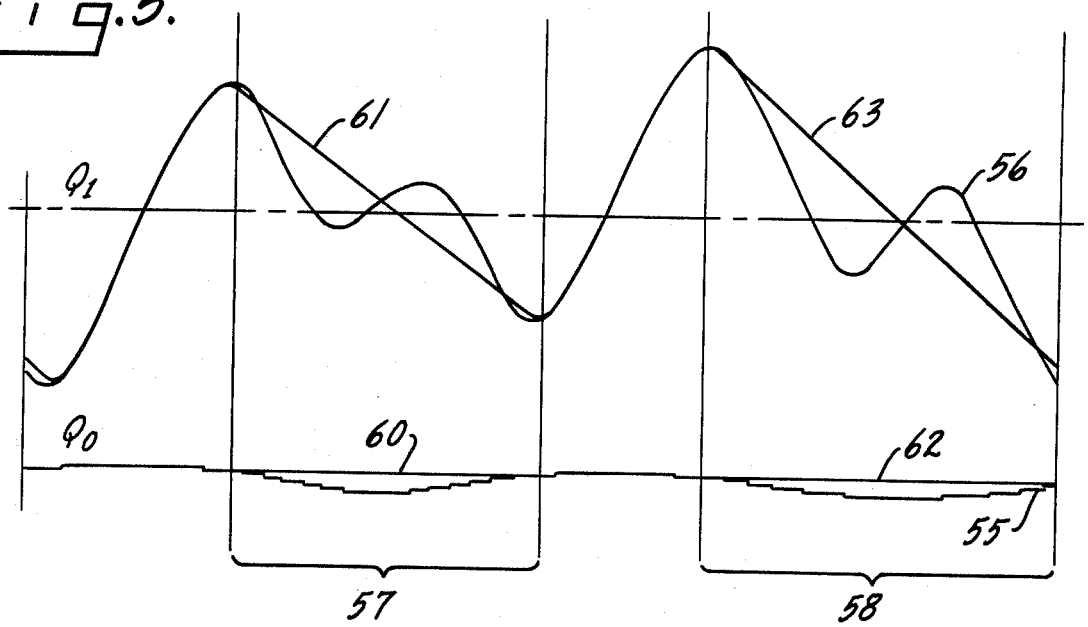

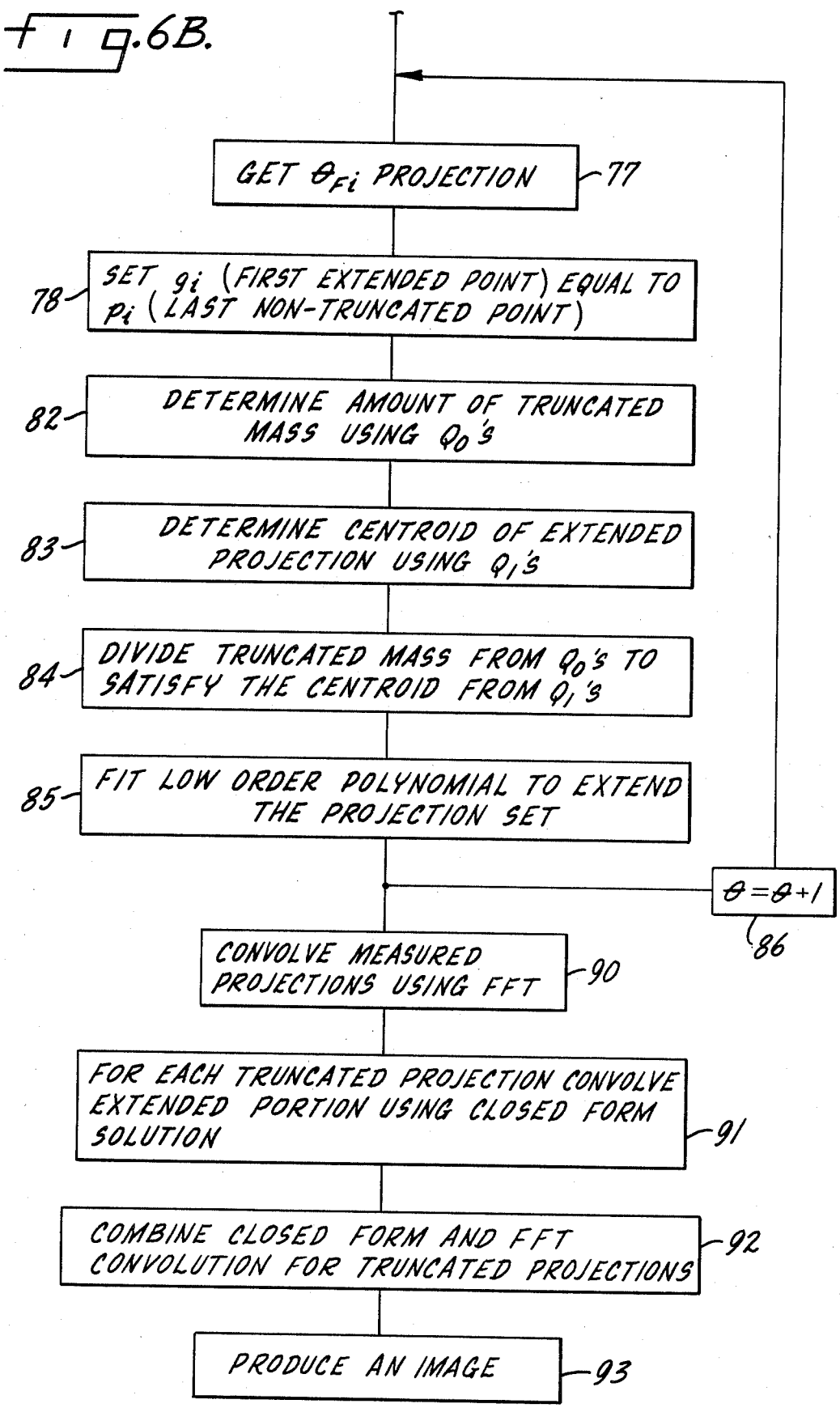

METHOD AND APPARATUS FOR COMPENSATING CT IMAGES FOR TRUNCATED PROJECTIONS

This invention relates to computed tomography and more particularly to a method and apparatus for reducing artifacts in CT images which result from an object extending beyond the scanner's field of view.

For a CT scanner to produce accurately reconstructed pictures it is necessary that the body being examined be confined within the scanner's field of view and that accurate reference channel data be available. The reference channels, typically adjacent to the channels that measure attenuation data, serve as monitors of the incident radiation beam intensity. The field of view is the area, typically circular, about which the source, or source and detector, rotate to expose the body and detect radiation from a plurality of angles around the body. If the body extends beyond the field of view, some of the measured projections are in error due to (a) shielding of the reference detectors thereby corrupting the reference channel information for some of the views and (b) failure to collect attenuation information concerning portions of the body extending beyond the field of view resulting in truncated views. For the former condition, the final image has low frequency shading resulting from improper reference level shifting. For the latter condition artifacts manifest themselves typically as low spatial frequency shading or cupping, and sometimes also as streaks.

For some kinds of scans, it is simply not possible to obtain the desired slice while assuring that the body remains within the field of view. For example, when scanning the upper portion of the torso of large individuals, it may not be possible to assure that the shoulders remain within the field of view.

In view of the foregoing, it is an aim of the present invention to minimize artifacts in images created from truncated projection sets.

In accomplishing that aim, it is an object of the present invention to identify projections having faulty reference information, and to improve that reference information before normalization.

A further object of the invention is to identify truncated projection sets and complete those sets with best estimate information derived from non-truncated sets. Finally, an object of the present invention is to accomplish the foregoing in an efficient manner which does not unacceptably increase the time needed to produce the CT image.

Other objects and advantages will become apparent from the following detailed description when taken in conjunction with the drawings, in which:

FIG. 5 illustrates the zeroeth and first order moments for a truncated set; and

FIGS. 6A and 6B are flowcharts illustrating the completion of truncated projection sets in practicing the present invention.

While the invention will be described in connection with certain preferred embodiments, there is no intent to limit it to those embodiments. On the contrary, the intent is to cover all alternatives, modifications and equivalents included within the spirit and scope of the invention as defined by the appended claims.

Figure 1:
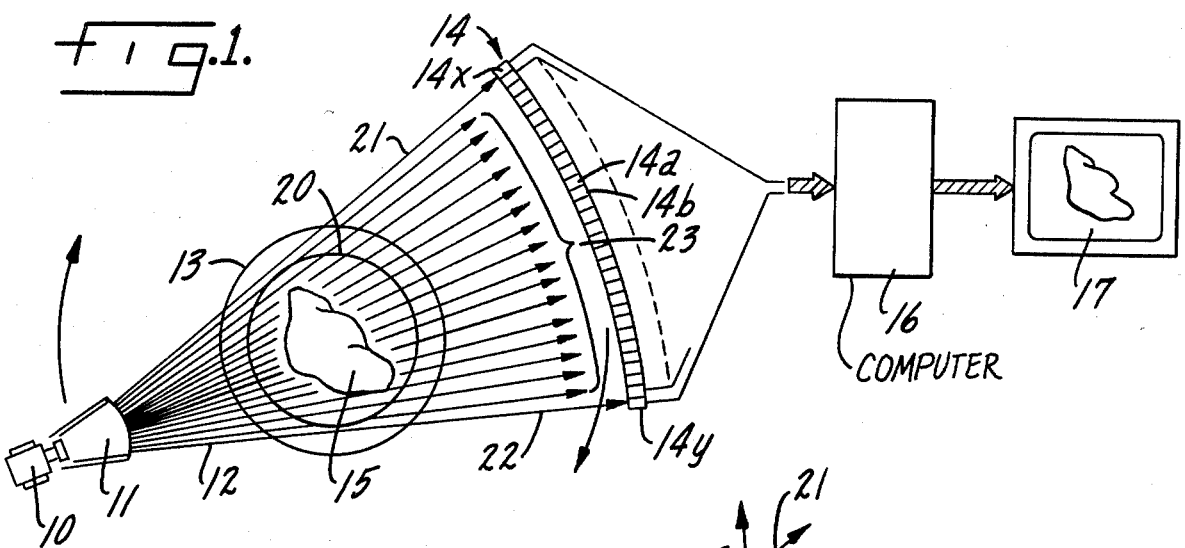
FIG. 1 is a schematic view illustrating the major elements of a CT scanner.

Turning now to the drawings, FIG. 1 schematically illustrates the major elements of a CT scanner. Note that a "rotate-only", or "third generation" scanner is shown for purposes of illustation, although the principles of this invention are not limited to such geometry. The scanner includes a source of penetrating radiation 10, very often in the form of a rotating anode X-ray tube. The radiation produced by the X-ray tube 10 is collimated at 11 to produce a thin fan beam of radiation 12 which is projected through a patient aperture 13 toward an X-ray detector array 14. A body to be examined, such as a patient 15, is positioned within the patient aperture 13 in the path of the fan beam of X-rays 12 such that the beam passing through the body is attenuated in dependence on the density of the objects encountered. As a result, each detector cell 14a, 14b, etc. produces an electrical signal which is dependent on the intensity of the radiation received within the cell. The signals thus produced are therefore measures of the attentuation of the X-ray beam by the portion of the body through which it passed.

In operation, X-ray readings are taken from each cell at a plurality of angular positions with respect to the patient, as the source and detector array are rotated about the patient aperture. Each set of readings at a particular angle is often referred to as a projection or view. A typical view for one available scanner is made up of 512 individual detector readings. Those readings for each view are digitized and fed to a reconstruction computer 16 which can use one of a number of available algorithms to produce the image of the cross section traversed by the fan beam. The image can be displayed on a CRT 17 or alternatively can be used to create a film for further study by a diagnostician.

A circle 20 within the patient aperture 13, and centered on the axis of rotation of the source and detector, represents the field of view for the geometry illustrated in FIG. 1. If accurate reconstructions are to be made, the patient 15 must be confined within the field of view 20, in order to first of all get reliable reference channel information and secondly to produce non-truncated projections.

In the illustrated embodiment, the end detector cells 14x, 14y of the detector array are not used for determining attenuation of the patient, but instead are used to produce reference readings characteristic of the unattenuated intensity of the X-ray source. Thus, it is important that radiation represented by the rays 21, 22, which pass through the patient aperture 13, but outside the field view 20, impinge on the cells 14x, 14y without interference. It is those readings which are used in the reconstruction computer 16 to normalize the readings from the remainder of the fan generally indicated at 23.

Figure 2:
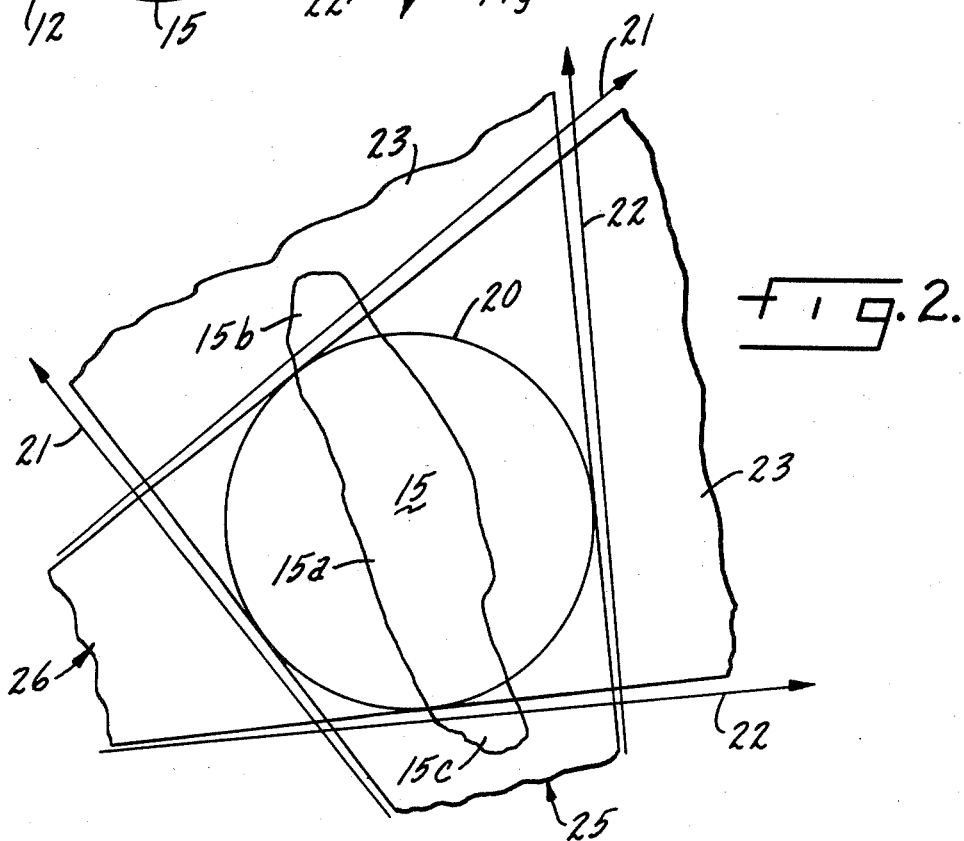
FIG. 2 is a diagram illustrating an object extending beyond the field of view.

FIG. 2 diagrammatically illustrates the problem. The field of view 20 is illustrated along with a body to be examined 15 having a portion 15a within the field of view, but portions 15b, 15c extending beyond that field. A pair of projections are illustrated at 25, 26. It is seen that the projection 25 is "normal" in that the reference rays 21 and 22 pass the field of view 20 unobstructed for receipt by their associated detector cells. Similarly, the entire body 15 is scanned in that the entire body passes radiation which will be detected.

However, the view 26 illustrates a projection which is truncated in two ways. First of all, both of the reference beams 21, 22 pass through the body such that the readings of the reference channels 14x, 14y will not be a true measure of the unattenuated intensity of the X-ray source for that view. Secondly, the attenuation of the entire body is not measured in view 26 because portions 15b and 15c are not within the field of view and, even if they were exposed to X-rays, those X-rays would not be detected. Thus, for the view 26, the scanner acts as if it were measuring a different body comprising only the section 15a.

The effect of the two conditions noted above can have a serious effect on the CT image if it were simply processed in the normal way. First of all, the obscuring of the reference channels for some of the projections causes each of those obscured projections to include a uniform d.c. shift. Such a d.c. shift tends to produce low frequency shading in any reconstruction made using the obscured projections. We have found that the d.c. shift caused simply by obscuring the reference channels can be on the order of 70 H.U. in typical clinical cases, a significant quantity.

Figure 3:
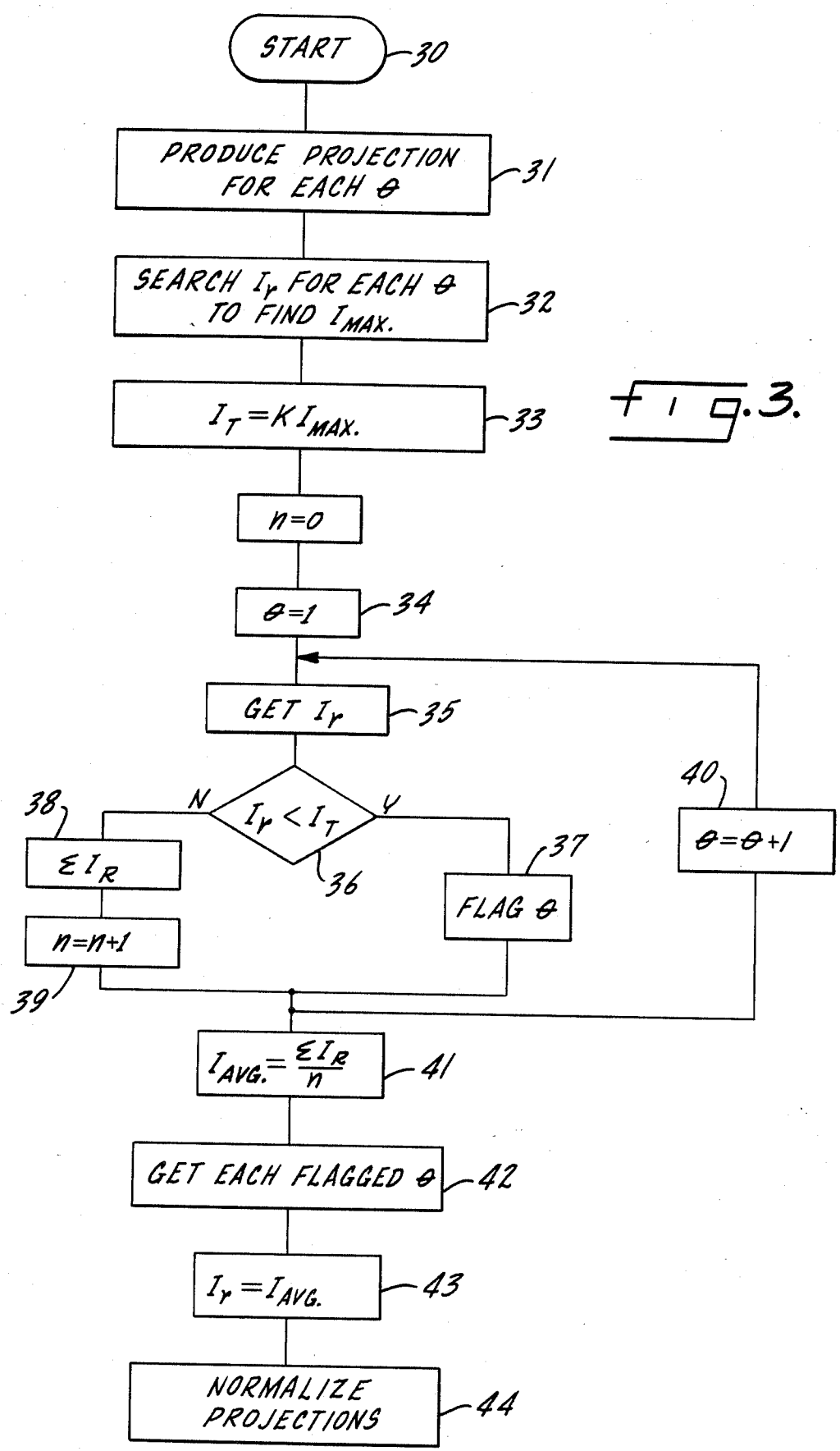
FIG. 3 is a flowchart illustrating the manner of improving reference channel information in accordance with the present invention.

In practicing the invention, the d.c. shift of the logarithmic projections for truncated views in which the reference channels were obscured is substantially reduced by identifying each view having obscured reference channel information and replacing it with better information derived from non-truncated projections. The manner in which that is accomplished is best explained with reference to FIG. 3, which illustrates a sequence of steps carried out within the apparatus of FIG. 1.

After starting the procedure at step 30, the apparatus is first cycled at step 31 to produce a projection or view for each angle $\theta$ as the source and detector rotate through a range of $\theta$'s around the patient. Scanners are available which can produce about 511 readings for each projection, and take approximately 576 projections as the source and detector rotate about the body. Each of those projections has reference cell intensity information associated therewith, referred to as $I_r$ in FIG. 3. Having produced all the projections at step 31, the system cycles to a step 32 which searches through each projection for the maximum intensity among all the reference channel information. Having acquired that maximum intensity information, the system determines a threshold intensity $I_T$ which is some fraction of the maximum intensity. Each reference intensity is then compared with the threshold so that the system can make a determination as to whether the reference channel for any view was likely obscured. As noted at 34, the first view is selected and at 35 the reference channel information obtained for that view. At step 36, the reference channel information is compared to the threshold intensity. If the reference channel is found to be below the threshold, a step 37 is used to flag that projection for later operation. If, on the contrary, the reference channel information is above the threshold, it is concluded that the view was made with unobscured reference channels. In that event, the intensity information is stored at a step 38 and an index incremented at 39 to produce typical reference information for later use. A step 40 is then used to select the next view and the procedure repeated. In each case, the view is either flagged at 37 or added to the summation at 38, depending on its relationship to the threshold intensity. After all views have been processed, a step 41 calculates a typical intensity, in the illustrated embodiment an average intensity, for the good views by dividing the summed intensity values by the number of values so summed. The program then at step 42 retrieves in turn each view or projection which had been flagged at step 37 and, for each of those views at step 43 replaces the reference intensity information with the average information calculated in step 41.

Having accomplished that for all views, the best reference channel information is then available and a step 44 can be accomplished to normalize each view in the conventional fashion.

We have found that processing the reference channel information in this way has proven to correct an error of about 70 H.U. by more than 50 H.U., thus proving to be of worthwhile benefit. A large part of the remaining error is due to the second type of aberration discussed above, namely, the presence of views in which portions of the body did not contribute to the projection set. That aspect of the problem can best be illustrated with reference to FIG. 4.

Figure 4:
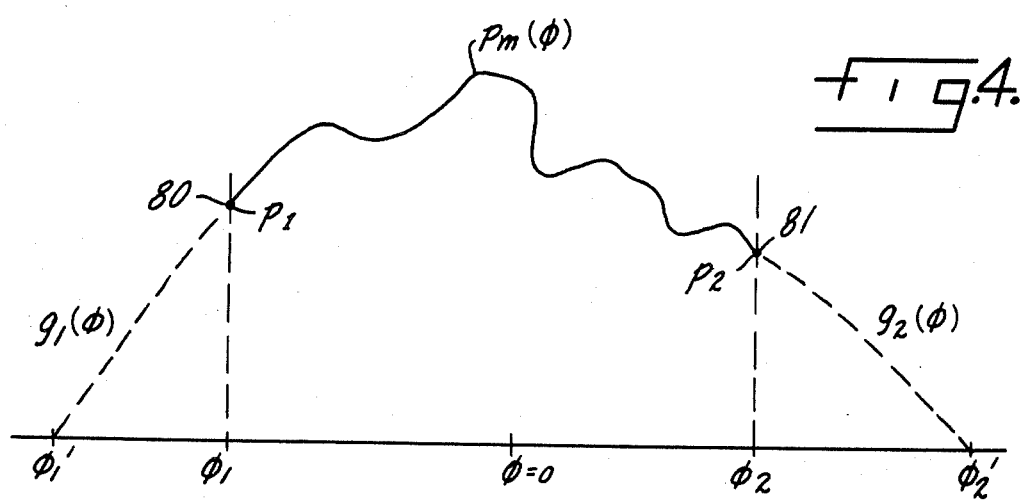
FIG. 4 is a diagram illustrating a truncated projection set.

FIG. 4 represents a plot of the measured logarithmic attenuation values for a view or projection. The amplitude is plotted along the vertical axis, and detector position within the fan is plotted as $\phi$ the horizontal axis. The central detector is illustrated in the center of the array at $\phi=0$. The plot is intended to illustrate a truncated view in that the detector itself encompasses only the fan angles from $\phi_1$ to $\phi_2$, $p_m(\phi)$ connoting values resulting from detector readings. The projection set is illustrated as extending beyond $\phi_1$ and $\phi_2$ to $\phi'_1$ and $\phi'_2$, respectively, and the functions $g_1(\phi)$ and $g_2(\phi)$ connote a truncated projection set. Recalling that the body portions 15b, 15c of FIG. 2 projected beyond the field of view, it will be appreciated that the $g_1(\phi)$ and $g_2(\phi)$ portions of the projection set have been lost. Thus, all the information derived in collecting the projection in question is represented by $p_m(\phi)$ and if that were convolved in the normal way, the fact that the $g_1(\phi)$ and $g_2(\phi)$ information was neglected would produce artifacts in the resulting image.

It is known that when the projections are truncated as in FIG. 4, that is, only the $p_m(\phi)$ information is available, it is impossible to uniquely reconstruct the object. However, if a reasonable number of the projections (say at least half) are not truncated, it is possible to make a reasonable estimate of the low spatial-frequency features of the "completion functions", the $g(\phi)$, and use that best estimate completed projection for further processing.

In practicing the invention, a plurality of moments of the projections, in the illustrated embodiment the zeroeth and first order moments, both truncated and non-truncated, are used to determine the degree of truncation, and to apportion the truncated information to the correction functions using, for each view, in addition to the moments, only information within the view in question.

Turning to FIG. 6A, it is seen that the system starts operation at 70, and first produces a projection set including all angles $\theta$ at step 71, in the manner described above. Step 72 is used to follow the entire procedure of FIG. 3 in removing the effects of obscured reference channels. Step 73 is then executed to determine the zeroeth and first order moments, $Q_0$ and $Q_1$ for each projection within the set. Digressing to FIG. 5, the nature of the moment of a projection set will briefly be discussed. The equation for calculating a moment is:

$$Q_k = \int_{\phi_1'}^{\phi_2'} p(\phi)\phi^k d\phi, \quad k = 0,1. \quad (1)$$

where Q is the moment, k is an index indicating its order, and the remaining variables have been previously identified. Thus, the zeroeth order moment is in the nature of an integration of the amplitudes in the projection p ($\phi$) and can be thought of as relating to the total "mass" within the projection. Since that mass doesn't change greatly if the entire object stays within the field of view, the zeroeth order moment should remain fairly constant for all views. For parallel beam geometry, the zeroeth order moment is indeed a constant whereas in the fan beam geometry illustrated in FIG. 1, the zeroeth order moment 55 can be a sinusoidal-like function with no more than one cycle across the set, and having relatively low amplitude. The first order moment is illustrated at 56, and can be conceptualized as related to the location of the centroid of the mass represented by the zeroeth order moment. Like the zeroeth order moment, it can vary with angle, but with only two full periods per 360 degree projection set.

In accordance with the invention, the moment information discussed above is examined to detect variations from expected behavior, to identify the views producing such variation as truncated, to estimate more likely moments for completed views, and to utilize that information in completing the truncated projections. FIG. 5 illustrates two areas where the moments behave in an unexpected fashion, those areas being bracketed at 57 and 58. It is seen that in the area 57, the amplitude of the zeroeth order moment $Q_0$ increases in an unexpected fashion and the initially well behaved first order moment $Q_1$ shows an unexpected undulation. Thus, each view encompassed within the area 57 can be said to be truncated, and expected moments should be determined to compare with the actual ones for the purpose of completing the views. Thus, for the zeroeth order moment, the more or less straight line segment 60 is determined to be a better estimate of what the moment of the completed data set would have been, and the straight line section 61 estimated to be a more likely first order moment for the area if the projection set had been complete. Similar criteria lead to the identification of the views bracketed at 58 as being truncated, and in the estimation of straight line 62 as a more likely zeroeth order moment and straight line 63 as a more likely first order moment for the area had the views been complete. While it is convenient to use straight lines, other curves could be used if desired.

Returning to FIG. 6, the step 74 performs the identification of the areas 57 and 58 and flags each view within those bracketed areas. The step 75 then determines what the moments would likely have been had the projection sets been complete as discussed above. Having made those determinations, the system then returns to each flagged view and, using the moment information detailed, above along with the information in that view, then completes the view by determining extension functions (the g ($\phi$)'s of FIG. 4). The latter is accomplished by fitting low order polynomials to the available information. The order of the polynomials chosen to represent $g_i(\phi)$ determines the number of constraints which must be formulated. That number in turn determines the number of moments which must be calculated in the formulation. The particular embodiment described here uses first-order polnomials (i.e., straight lines), for which only $Q_0$ and $Q_1$ need be considered.

In order to determine the coefficients of the particular low order polynomials, a first constraint is placed on the extended projection set, requiring at some point that its amplitude go to zero. That is likened to the physical requirement of the body ending at some point. FIG. 4 illustrates the points $\phi'_1$ and $\phi'_2$ at which the extended projection set goes to zero. The actual location of $\phi'_1$ and $\phi'_2$ must still be determined.

An additional two constraints are placed on the function using the zeroeth and first order moments. Having determined best estimate values for those moments above, and knowing the actual moments for the truncated projection sets, the requirement is that the measured moments be altered to conform with the expected moments.

A final constraint found useful is that of continuity of the projection and its derivatives across boundaries between the truncated projection set and the extended projection set. That can be stated as the derivative of some order of $g_i$ with respect to $\phi$ equal to the derivative of $p_i$ with respect to $\phi$ at $\phi_1$ and $\phi_2$. The order of the derivatives required for this constraint is determined by the order of the polynomial. If a first order polynomial, i.e., a straight line, is chosen, then it is only necessary to insure that the completed projection is continuous at the boundary. Continuity can be accomplished by simply assigning the amplitude of the last point in the truncated set, $p_1$ or $p_2$, to the first point in the extended set $g_1$ or $g_2$, respectively.

Turning to FIGS. 6A and 6B, it is seen that the steps 76, 77 serve to obtain the first truncated view (that which would correspond to $p_m(\phi)$ of FIG. 4). The step 78 is then accomplished as described generally above to set the value of the first point in the extended projection set to that of the last point in the truncated projection set at each end of the set. The points where that operation is accomplished are illustrated at 79, 80 of FIG. 4.

The system then proceeds to a step 82 which determines the amount of mass which was truncated by using the zeroeth order moment information. More particularly, recalling FIG. 5, and assuming the system is operating on a view within the bracketed portion 57, the system would determine the difference between the estimated zeroeth order moment 60 and the corresponding measured moment from the truncated data.

Step 83 is then performed to determine the centroid of the total amount of mass in the extended projection set using the first order moment information from step 75. The physical significance of that can be appreciated with respect to FIG. 4. Recalling that the points 80 and 81 are known, the step 82 determines the total area under the curves $g_1(\phi)$ and $g_2(\phi)$. In order to further define those functions, the step 83 determines where the center of mass for the entire projection set should be, and from that information the area under the curves $g_1(\phi)$ and $g_2(\phi)$ can be apportioned. That is accomplished in a step 85 by fitting a low order polynomial to the extended projection set, thus defining in the illustrated embodiment $g_1(\phi)$ and $g_2(\phi)$ by requiring them to be straight lines, and by determining their slope and intercept. A step 86 then selects the next truncated projection and repeats the entire procedure. The end result is the completion of each truncated projection with estimated data most likely to satisfy at least the low frequency continuity requirements of the reconstruction algorithm.

The manipulative steps set out in connection with FIGS. 6A and 6B can also be described mathematically, and a discussion thereof will be provided as an aid in programming the reconstruction computer to perform the method according to the present invention. First of all, the straight line to be defined for the extended function, $g_1(\phi)$ or $g_2(\phi)$, or generally $g_i(\phi)$ where i is 1 or 2, can be defined as:

$$g_i(\phi) = a_i\phi + b_i, \tag{2}$$

The coefficients $a_i$ and $b_i$ are to be determined in order to define the function. The continuity of the projection requires that:

$$g_i(\phi_i) = p_m(\phi_i) = p_i, \tag{3}$$

which states mathematically that the truncated curve connects smoothly with the extended curve at the points 80 and 81 of FIG. 4. It follows from that requirement that the value of $\phi_i$ at 0 amplitude is defined by:

$$\phi'_i = -b_i/a'_i, \tag{4}$$

With that in mind, equation (3) can be rewritten as:

$$g_i(\phi) = a_i(\phi - \phi_i) + p_i. \tag{5}$$

In addition, a function $\delta_i$ can be defined, relating to the horizontal coordinate of the extension function ($\phi'_i - \phi_i$), and that can be set equal to the intercept and slope as set out in equation 4 yielding the following:

$$\delta_i = \phi'_i - \phi_i = -p_i/a_i. \tag{6}$$

The steps 82 and 83 of FIG. 6 can be described mathematically by the following expression:

$$R_k = Q_k - \int_{\phi_1}^{\phi_2} p_m(\phi)\phi^k d\phi = \int_{\phi_1'}^{\phi_1} \theta_1(\phi)\phi^k d\phi + \int_{\phi_2}^{\phi_2'} \theta_2(\phi)\phi^k d\phi, \tag{7}$$

where the expression generally applies to moments of all orders, but the zeroeth and first order moments are utilized by setting the index k equal to zero and 1. The quantity $R_k$ is the difference between the moment of the truncated set and the expected moment had the set been complete. The quantity $Q_k$ represents the latter, whereas the integral of $p_m$ between the limits of $\phi_1$ and $\phi_2$ represents the measured moment from the truncated data set. That difference is the quantity which must be divided between the extension functions, as set out for the $g_1(\phi)$ and $g_2(\phi)$ integrals over the extended function.

Equation 18 can be manipulated to yield a form more adaptable to utilizing the moment and view information in determining the coefficients of the extended function. After some manipulation, and utilizing both the zeroeth and first order moments, equation 7 leads to:

$$\frac{p_1^2}{2} \xi_1 - \frac{p_2^2}{2} \xi_2 = R_0 \tag{8}$$

$$\frac{\phi_1 p_1^2}{2} \xi_1 - \frac{p_1^3}{6} \xi_1^2 - \frac{\phi_2 p_2^2}{2} \xi_2 + \frac{p_2^3}{6} \xi_2^2 = R_1, \tag{9}$$

$$\xi_i \equiv 1/a_i \tag{10}$$

Elimination of $\xi_1$ leads to:

$$V_1 \xi_2^2 + V_2 \xi_2 + V_3 = 0, \tag{11}$$

where:

$$V_1 = \frac{p_2^3}{6}(1 - p_2/p_1) \tag{12}$$

$$V_2 = \frac{p_2^2}{2}\left(\phi_1 - \phi_2 - \frac{4}{3}\frac{R_o}{p_1}\right)$$

$$V_3 = -R_1 + \phi_1 R_o - \frac{2}{3}\frac{R_o^2}{p_1}$$

Using the conventional formula for solution of a quadratic, and solving equation 11 for $\xi_2$ yields:

$$\xi_2 = \{-V_2 - \sqrt{V_2^2 - 4V_1V_3}\}/2V_1 \tag{13}$$

finally, using $\xi_2$ to solve for $\xi_1$, the inverse of the slope of the extended function, yields:

$$\xi_1 = \frac{p_2^2}{p_1^2}\xi_2 + \frac{2R_0}{p_1^2}. \tag{14}$$

Having first determined the actual truncated moments and expected moments had the projection in question not been truncated, it will now be apparent that any view can be accessed and completed simply using the moment information and the data from the view in question. First of all, it is first necessary to use the amplitudes of the points 80 and 81 (FIG. 4) identified as $p_1$ and $p_2$, the zero and first order moments $R_0$ and $R_1$, and the channel angle at truncation $\phi_1$ and $\phi_2$ to compute the coefficients set out in equation 12. Those coefficients are then used in equation 13 to calculate $\xi_2$ following which $\xi_2$ is used in equation 14 to calculate $\xi_1$. The intercepts are provided by equation 4, and using only the information within that view, the coefficients for the functions $g_1(\phi)$ and $g_2(\phi)$ are determined to complete the truncated data set.

It is noted that a special case can exist where the projection is truncated on only one side. In that case, it is only necessary to apply equation 3 and the first moment Equation (7) to find the slope. In the case where the left end of the projection is missing, the inverse of the slope is determined by:

$$\xi_1 = 2R_0/p_1^2, \tag{15}$$

while for the right end:

$$\xi_2 = -2R_0/p_2^2. \tag{16}$$

Thus, the coefficients of the two extension functions are completely determined, and in combination with the original truncated projection defines an extended projection which will satisfy at least the low frequency continuity requirements of the reconstruction algorithm.

It is then possible to use that extended function by convolving it with the standard convolution filter to produce a filtered data set used in back projection to reconstruct an image. However, in many modern CT scanners, convolution is performed in the Fourier domain, first using a Fast Fourier Transform followed by a multiplication and an inverse transform before back projection.

In a particular CT scanner, a 1024 point FFT is used on non-truncated data sets having about 511 elements to avoid wrap-around. It is thus not unlikely to assume that extending a projection set as described above will increase the data set such that a 1024 point FFT will not be sufficient. To use standard convolution techniques for that extended data set would therefore require at least a 2048 point FFT, approximately doubling the time necessary to make the transform.

In accordance with a particular aspect of the invention, that difficulty is avoided by using conventional FFT convolution for the non-truncated portion of the data set and using an approximate closed form solution for the extended portion, then combining the two convolutions to produce a modified projection set for back projection. Thus, returning to FIG. 6B, a step 90 convolves each of the measured projection sets whether truncated or not. Then, a step 91 selects each of the truncated sets and performs a closed form solution for convolution of the extension. A step 92 then combines that closed form convolution with the FFT convolution of step 90 for each truncated projection set in order to produce a more accurate set of filtered data taking into account the body portions beyond the field of view. The step 93 then performs the normal procedures used for producing an image, typically back projection.

The convolution of the extended portion, which it is desired to evaluate can be set out as follows:

$$q_i(\phi) = [g_i(\phi)\cos\phi] * K(\phi), \quad \phi_1 < \phi < \phi_2, \quad (17)$$

where $K(\phi)$ is the kernel, and the expression need only be evaluated within the field of view, that is, between $\phi_1$ and $\phi_2$. When a specific kernel is chosen, in the present example that which has come to be known as the LAKS kernel, equation 17 can be evaluated in closed form. First of all, it can be approximated as:

$$q_i(\phi) = \cos\phi_i [g_i(\phi) * K(\phi)]. \quad (18)$$

Then for:

$$g_2(\phi) = p_2\left(1 - \frac{\phi - \phi_2}{\delta_2}\right), \quad (19)$$

the Fourier transform is:

$$G_2(k) = p_2 e^{-ik\phi_2}\left\{\frac{1 - \cos k\delta_2}{k^2\delta_2} + i\left(\frac{\sin k\delta_2}{k^2\delta_2} - \frac{1}{k}\right)\right\} \quad (20)$$

Thus, for the LAKS kernal the convolution can be stated as:

$$q_2^1(\phi) = \frac{q_2(\phi)}{p_2\cos\phi_2} = \frac{1}{2\pi} \cdot \int_{-\infty}^{\infty} |k| G_2(k)e^{ik\phi}dk \quad (21)$$

and can be solved as:

$$q_2(d) = \frac{1}{\pi\delta_2} \log\left[\frac{\delta_2 + \phi_2 - \phi}{\phi_2 - \phi}\right] - \frac{1}{\pi(\phi_2 - \phi_1)} \quad (22)$$

for the limits within the field of view. A similar expression can be calculated for $q_1$, evaluating the effect on the convolution of the area outside the field of view on the elements within the field of view.

The use of "LAKS" kernel for fan-beam geometry is not strictly valid. We have found that the error so produced is negligible inasmuch as only low spatial frequencies are recovered by the extension process.

Experimentation with the procedures described herein, in which the first two moments of the extended projections are made consistent with the other views, has shown that shading artifacts caused by truncated views can be significantly reduced. Furthermore, using the closed form solution for evaluation of the convolution of the extensions of the projection sets accomplishes that result without an unacceptable increase in processing time.

We claim as our invention:

1. A method of compensating a CT image comprising the steps of exposing a body to radiation at a plurality of angles about the body, detecting radiation passing through the body at the plurality of angles to create a set of projections, each of the projections including reference channel information indicative of the unobstructed X-ray source density for normalizing the associated projection but in which some of said projections are effected by the body extending beyond the field of view to obstuct the reference channels; analyzing the reference channel information to detect reference channel information below a predetermined level and thereby identify the projections having reference channel information affected by the object, determining a typical reference channel level representative of the projections having reference channel information unaffected by the object from the unaffected projections, assigning the typical reference channel level to the reference channels of said identified projections, normalizing each projection with the reference level assigned thereto, and producing an image from the normalized projection set.

2. A method of compensating a CT image comprising the steps of exposing a body to radiation at a plurality of angles about the body, detecting radiation passing through the body at the plurality of angles to create a set of projections, each of the projections including reference channel information indicative of the unobstructed X-ray source intensity for normalizing the associated projection but in which some of said projections are affected by the body extending beyond the field of view to obstuct the reference channels; finding the maximum reference channel level within the projection set, identifying each projection having a reference channel level which is a predetermined amount less than said maximum level thereby to identify the projections having reference channel information affected by the object, determining a typical value of reference channel level representative of the projections having reference channel information unaffected by the object for projections not identified, replacing the reference channel level in the identified projections with said typical value, normalizing each view with respect to the reference level assigned thereto, and producing an image from the modified projection set.

3. The method as set out in claim 1 or claim 2 in which some of the projections are truncated, further comprising the steps of determining the zeroeth and first order moments of the projection set, determining from the zeroeth order moment the amount of missing mass from the truncated projections, determining from the first order moments the centroid of an extended projection relating to each truncated projection, using the missing mass and centroid information for each truncated projection to extend said projection, convolving each projection to produce a convolved projection set, and producing an image from the convolved projection set.

4. The method as set out in claim 3 wherein the step of convolving includes using a Fast Fourier Transform to convolve each untruncated projection and the non-truncated portion of each truncated projection, using a closed form solution to convolve the extended portions of the truncated projections, and combining the closed form solution with the convolution for each truncated projection set.

5. A method of compensating a CT image comprising the steps of exposing a body to radiation at a plurality of angles about the body, detecting radiation passing through the body at the plurality of angles to create a set of projections, some of said projections being truncated by the body extending beyond the field of view, determining a plurality of moments of the projection set, determining from the moments the amount of mass missing from each truncated projection and the distribution of the missing mass in each truncated projection, fitting a low order polynomial conforming with the moments and boundary conditions to extend each truncated projection, convolving each projection with a kernel to produce a convolved projection set and producing an image from the convolved projection set.

6. The method as set out in claim 5 wherein the step of determining a plurality of moments includes determining the zeroeth and first order moments, the step of determining the amount of missing mass uses the zeroeth order moment, and determining the distribution of the missing mass uses the first order moment.

7. The method as set out in claim 5 wherein the step of convolving includes using a Fast Fourier Transform to convolve each untruncated projection and the non-truncated portion of each truncated projection, using a closed form solution to convolve the extended portions of the truncated projections, and combining the closed form solution with the convolution for each truncated projection.

8. The method as set out in claim 5, 6 or 7 in which the step of fitting a low order polynomial includes starting the extended portion at a point smoothly merging into the non-truncated portion of the projection, using the zeroeth and first order moments to fit the low order polynomial between the starting point and a point at which the extended projection becomes zero.

9. The method as set out in claim 8 in which the low order polynomial is a first order polynomial.

* * * * *